United States Patent [19]

Toet et al.

[11] Patent Number: 5,330,912

[45] Date of Patent: Jul. 19, 1994

[54] **PRODUCTION OF *TRICHODERMA HARZIANUM* RIFA CMI CC NO. 333646**

[75] Inventors: Mary J. Toet; Amanda Somers, both of Harare, Zimbabwe

[73] Assignee: Agricura (Private) Limited, Zimbabwe

[21] Appl. No.: 904,351

[22] Filed: Jun. 25, 1992

[30] Foreign Application Priority Data

Jul. 1, 1991 [ZW] Zimbabwe ............... 87/91

[51] Int. Cl.⁵ ............................................. C12N 1/14
[52] U.S. Cl. ................................. 435/254.1; 435/945
[58] Field of Search ....................... 435/254, 945

[56] References Cited

U.S. PATENT DOCUMENTS

| | | | |
|---|---|---|---|
| 3,013,946 | 12/1961 | Lumb et al. | 435/254 |
| 4,489,161 | 12/1984 | Papavizas | 435/254 |
| 4,574,083 | 3/1986 | Baker et al. | 435/254 |
| 4,797,361 | 1/1989 | Montenecourt | 435/945 |
| 4,837,155 | 6/1989 | Tabachnik | 435/254 |
| 4,950,472 | 8/1990 | Janisiewicz | 424/93 |
| 4,996,157 | 2/1991 | Smith et al. | 435/254 |
| 5,068,105 | 11/1991 | Lewis et al. | 424/93 |

*Primary Examiner*—David M. Naff
*Assistant Examiner*—Deborah K. Ware
*Attorney, Agent, or Firm*—Davis, Bujold & Streck

[57] ABSTRACT

The invention provides a process for production of *Trichoderma harzianum* Rifa T77 deposited as CMI CC. No. 333646 on a commercial scale. The process involves loading receptacles with culture medium; sterilization of the medium in situ; inoculating the sterilized medium with spores of T77; incubating the inoculated for 21 days at 29 degrees centigrade; cooling; and packaging under ambient conditions.

3 Claims, 1 Drawing Sheet

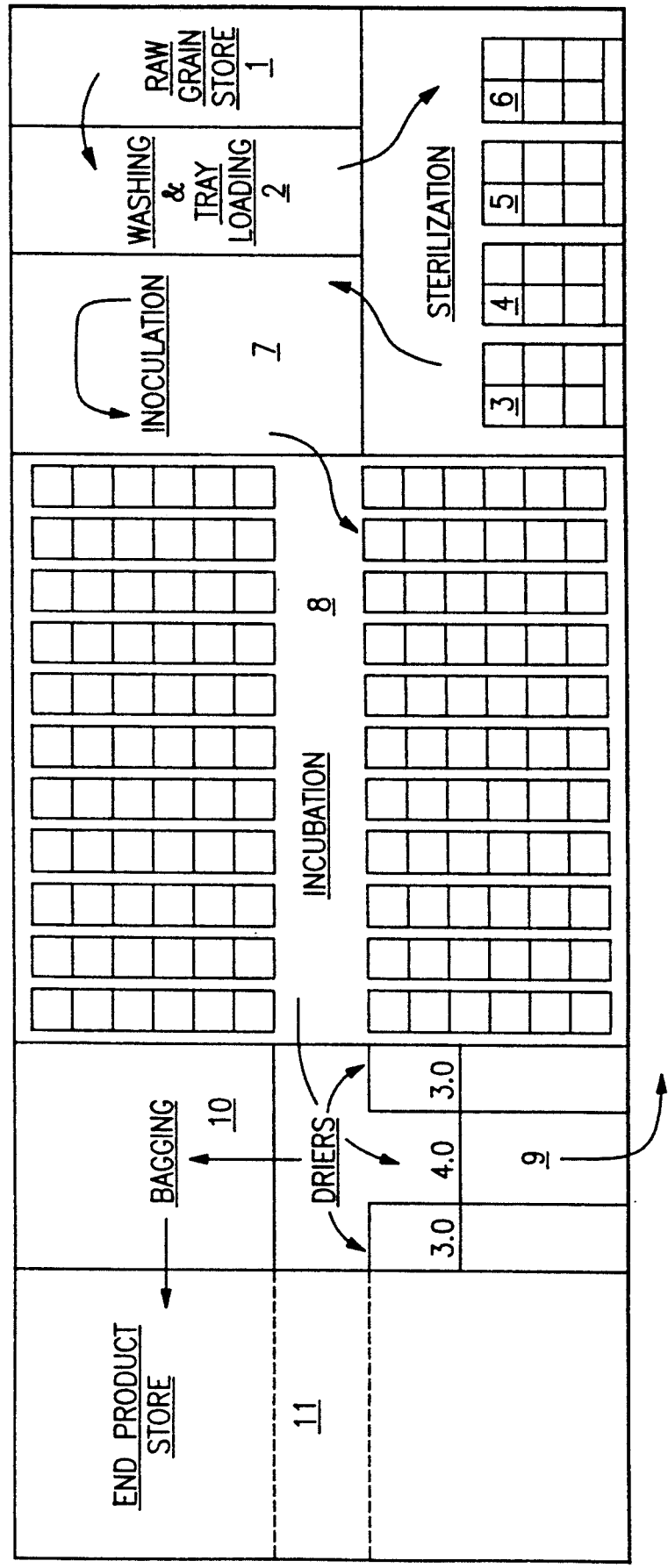

PRODUCTION OF *TRICHODERMA HARZIANUM* RIFA CMI CC NO. 333646

BACKGROUND OF THE INVENTION

This invention relates to the bulk production of *Trichoderma harzianum* Rifa and more particularly to the T77 strain.

The T77 strain of *Trichoderma harzianum* Rifa is known from Zimbabwe Patent no. 104/89 granted to the Tobacco Research Board of Zimbabwe and its pathology has been described therein. The microorganism *Trichoderma harzianum* Rifa strain T77 is identified as CMI CC Number 333646 by CAB International Mycological Institute, Ferry Lane, Kew Surrey TW9 3AF, United Kingdom where the organism has been deposited, for the purposes of patent procedures under the Budapest Treaty, CMI culture collection being an International Depository authorized under the Treaty, and was there tested as being viable. The deposit was received by the CAB International Mycological Institute on Jul. 3, 1989 and accepted for deposit on Jul. 18, 1989.

It is an object of this invention to produce *Trichoderma harzianum* Rifa T77 on a commercial scale for general use. This microorganism is useful when added to soil in suitable conditions for it to multiply and grow in close association with plants' roots to partially protect them from invasion by certain plant pathogenic fungi and to stimulate plants' growth.

SUMMARY OF THE INVENTION

According to the invention, a process for the production of strain T77 of *Trichoderma harzianum* Rifa includes the steps of preparing a culture medium consisting of about 1 part spent grain, about 1 part water and about 0.06 parts molasses; sterilizing the culture placing the sterilized culture medium in a receptacle; inoculating the sterilized culture medium with T77 spores; incubating the inoculated culture at about 29 degrees centigrade for about 21 days; drying the resultant growth for five to seven days at ambient temperatures in sterile conditions and packaging the product for sale.

Spent grain may be replaced by other carriers, such as crushed maise cobs; bran; cellulose (such as coffee waste); bagasse, peat or brick dust with 4.2% by weight of sugar added and the PH kept between 4 and 5.

Also according to the invention, the culture medium may be sterilized by the Tyndalisation procedure wherein culture medium is spread over trays having presently preferred dimensions of height 16 cms, breadth 50 cms and length 80 cms, the trays then being placed in a heating chamber and subjected to heated air at 130–140 degrees centigrade for 24 hours followed by a cooling period of 24 hours and a re-heat at 130–140 degrees centigrade for a further 24 hours; the sterile culture medium in the trays then being inoculated by known means with T77 spores followed by incubation for 21 days at but 29 degrees centigrade whereafter the product is dried under ambient conditions for from 5 to 7 days and packaged.

BRIEF DESCRIPTION OF THE DRAWINGS

The invention will now be described, by way of example, with reference to the accompanying drawing which depicts diagrammatically a full scale production plant.

DESCRIPTION OF THE PREFERRED EMBODIMENT

Example I

In a first example of possible commercial manufacture, glass tomato sauce bottles of 75 mm size hexagonal shape were procured and filled with culture medium made up in 5 kilogram batches consisting of spent grain, water and molasses in the ratio 5 kilograms to 5 kilograms (liters) to 282 grams respectively. The bottles were then plugged with cotton wool and covered with a grease proof paper whereafter they were sterilized for twenty minutes at 121 degrees centigrade and allowed to cool before being inoculated with *Trichoderma* T77 spores.

The spores were harvested from a Sabouraud Dextrose agar plate by washing the plate with 20 milliliters of sterile distilled water. Each bottle was inoculated with 2 milliliters of the inoculum using a sterile plastic syringe. The spore count was in excess of one times ten to the power six spores per milliliter.

After inoculation, the bottles were put in an incubator which in this instance was a "modro" (mobile tobacco bulk curer) made by Modro Manufacturers (Private) Limited in which incubator the temperature was controlled by an air conditioner and maintained at 29 degrees centigrade, plus or minus 1 degree centigrade, for twenty one days covering the growth period.

The bottles were then emptied onto a plastic sheet in the modro and dried for about five to about seven days under ambient conditions. Problems were encountered with this method in that it was labour intensive and produced rather a low yield, each bottle harvesting approximately 150 to 200 grams of dried *Trichoderma*. In addition it was found that the bottles began to break after being autoclaved twice and the very limitation of autoclaving a number of bottles in a small apparatus limited the production capacity of this particular method.

Example II

In this example, both aluminum and steel trays were manufactured dimensions of 16 cms in height by 50 cms breadth and 80 cms length and these trays were filled with non-sterile culture medium in the ratio used in Example I. After charging the trays with medium, sterilization was initiated by Tyndalisation within the modro where the temperature was raised to 150 degrees centigrade for twelve hours; allowed to cool down for 24 hours and then re-heated to 150 degrees centigrade for a further twelve hours. The sterile medium was then inoculated with *Trichoderma* T77 spores harvested from a Sabouraud Dextrose Agar, plate system using a plastic sterile syringe to get a good distribution of the spores over the tray. The trays were left in the air conditioned modro at 29 degrees, plus or minus 1 degree centigrade, for 21 days to cover the growth period.

It was found that growth appeared to best in those trays where the medium was deepest, but a good average depth was about 16 cms.

Certain problems were experienced, notably by way of contamination of the trays by other species of fungus, particularly around the edges of the tray and at the corners which may well not have been too well formed or sealed during manufacture. During this experiment, the trays had been covered by a sheet of glass and some sealing had been effected by adhesive tape, but it was found in subsequent repeats of this particular example that *Trichoderma* T77 does not require light for growth so that future trays will be provided with a metal lid which can be clamped down into a better sealing relationship with the body of the tray.

A further problem encountered in experimental trays made of galvanized steel seems to indicate that there might be an attack upon the material of the trays during the growth period.

Example III

Trays were manufactured from stainless steel provided with substantially airtight sliding stainless lids. Contamination was reduced to negligible proportions and yields increased to near theoretical being about 3 tons per modro per cycle period.

Based upon the Examples a full-scale plant was constructed and a plan of this plant is depicted in the accompanying drawing.

In the illustrated plant, raw growth medium is drawn from a bulk store 1 (holding 14 tonnes 2 meters deep with an area of 44 square meters) and passed to a washing and filling area 2 where the medium is mixed by mechanical means. Trays are filled and loaded, 48 to a trolley to make up a six trolley batch. One batch of six trolleys with trays moves through the system daily.

Four sterilization chambers 3, 4, 5, 6 are provided, each capable of accepting one batch, and a four day tyndalisation regimen is observed. Heat, for the process is derived from a boiler and ducting assembly capable of servicing the chambers on a continuous basis. Heating takes place in the chambers for an initial 24 hour period at temperatures of 130–140 degrees centigrade followed by cooling periods of 24 hours, which cooling is expedited by means of heat-exchangers in each chamber resulting a heat-transfer gain as well as effective tyndalisation. The first heating/cooling cycle is followed by a second 24 hour/24 hour period whereafter the batch progresses to an inoculation chamber which is under positive air pressure during use.

Inoculation comprises removal of the trays from the trolleys onto a conveyor and removal of the tray lids. An automatic metered pumping system of conventional design then ensures that the sterile medium in each tray is sprayed with spores of T77 in the inoculation chamber 7. Trays are re-covered with their lids and replaced in the trolleys whereafter the batch is transferred to the incubation room 8 which is also maintained under positive air pressure when in use.

Incubation takes place under strictly controlled conditions of temperature. The optimum temperature is 29 degrees centigrade but variations of 1 degree centigrade each side of the optimum may be tolerated. The period of incubation is 21 days per batch whereafter the batch will have progressed through the bays in the incubation room and are then transferred to the cooling and drying room 9 where trays are uncovered and the contents emptied into drying racks. Drying takes place in a cool stream of sterile air derived in conventional manner from ambient.

After the T77 has cooled and dried over a period of five to seven days it is bagged in the bagging room 10 and stored in store 11 (in which 300 tonnes of T77 occupies 469 square meters 2 meters deep) at temperatures below 20 degrees centigrade until required for use in the field.

We claim:

1. A method for producing *Trichoderma harzianum* Rifa strain CMI CC No. 333646 in a form suitable for adding directly to soil to protect plants from pathogenic fungi comprising the steps of:
   1) preparing a carrier-containing culture growth medium comprising a carrier, water and molasses, said carrier being selected from the group consisting of spent grain, crushed maize cobs, bran and cellulose;
   2) sterilizing the carrier-containing culture growth medium by a Tyndalisation procedure comprising the steps of:
      a) spreading the carrier-containing culture growth medium over trays,
      b) placing the trays in a heating chamber and
      c) heating said chamber to a temperature of from about 130° C. to about 140° C. for about 24 hours and
      d) cooling for about 24 hours and
      e) reheating to about 130° C. to about 140° C. for about 24 hours;
   3) inoculating the sterilized carrier-containing culture growth medium with *Trichoderma harzianum* Rifa strain CMI CC No. 333646 spores;
   4) incubating the inoculated and sterilized carrier-containing culture growth medium at about 28° C. for about 21 days to grow the *Trichoderma harzianum* Rifa CMI CC No. 333646 to form an incubated product; and
   5) drying the incubated product in a sterile air stream at ambient temperature to obtain said *Trichoderma harzianum* Rifa strain CMI CC No. 333646 for adding directly to soil to be protected.

2. A method according to claim 1, wherein the carrier is spent grain and the carrier-containing culture growth medium consists of, by weight, about 1 part spent grain, about 1 part water and about 0.06 parts molasses.

3. A method according to claim 1, wherein the carrier-containing culture growth medium comprises about 1 part spent grain, about 1 part water and about 0.056 parts molasses.

* * * * *